US00PP11118P

United States Patent [19]

Andersen et al.

[11] Patent Number: Plant 11,118

[45] Date of Patent: Nov. 9, 1999

[54] SWEET CHERRY CULTIVAR NAMED 'SOMERSET'

[75] Inventors: Robert L. Andersen; Susan K. Brown, both of Geneva; Roger D. Way, Stanley; Kenneth G. Livermore, Geneva; David E. Terry, Ovid, all of N.Y.

[73] Assignee: Cornell Research Foundation, Inc., Ithaca, N.Y.

[21] Appl. No.: 08/876,370

[22] Filed: Jun. 13, 1997

Related U.S. Application Data

[63] Continuation of application No. 08/654,785, May 28, 1996, abandoned, which is a continuation of application No. 08/148,084, Nov. 4, 1993, abandoned.

[51] Int. Cl.[6] ..... A01H 5/00

[52] U.S. Cl. ..... Plt./181

[58] Field of Search ..... Plt./37, 181, 182, Plt./183

[56] References Cited

PUBLICATIONS

A Catalog of New and Noteworthy Fruits, 1980–1981, New York State Fruit Testing Cooperative Association Geneva, New York 14456, p. 10.

Fruit Varieties Journal, A Publication of American Pomological Society, Jul. 6, 1993, vol. 47, No. 3, pp. 168–171.

*Primary Examiner*—Howard J. Locker

[57] ABSTRACT

A new distinctive cultivar of sweet cherry (*Prunus avium*) named 'Somerset' (formerly tested as NY 6476) which is exceptional in combining 1) firm, highly attractive fruit that resist rain induced fruit cracking, 2) a tree habit that branches more profusely than many other cultivars and which facilitates precocious cropping, and 3) having a unique affinity of genetic compatibility with some hybrid cherry rootstock cultivars that cause genetic incompatibility and early decline in many other scion cultivars.

3 Drawing Sheets

CROSS-REFERENCE TO RELATED APPLICATIONS

This is a continuation of U.S. application Ser. No. 08/654,785, filed May 28, 1996, now abandoned, which is a continuation of U.S. application Ser. No. 08/148,084, filed Nov. 4, 1993, now abandoned.

BACKGROUND OF THE INVENTION

In 1960 hybrid cherry seeds created from controlled pollinations between 'Van' X 'Vic' were harvested at the New York State Agricultural Experiment Station (Station). These seeds were given cold treatment to satisfy their stratification requirement along with other seed derived from our cherry breeding research. In 1961 the population of 'Van' X 'Vic' seedlings designated as Breeding Record 59433 were planted. This population included a tree located at a site designated as Darrow 3 Row 14 Tree #83 (D3R14T83). This tree bore fruit in 1966 that we observed to have exceptional firmness and skin that is more shiny (glossy) and blacker than the skin of most other dark fleshed, dark skinned sweet cherry cultivars. It was designated NY 6476 and grafted in 1967 to 'Mazzard Seedling' sweet cherry rootstocks utilizing the nursery t-budding grafting technique. These grafts produced trees to be used for more tests of this selection's merit. Grafted trees that resulted were planted in 1969 in a Station field designated as Lucey R1T26 and Lucey R2T27. In 1973 further grafted trees resulted from using Lucey R2T27 buds for propagating wood and planting trees grafted to 'Mazzard Seedling' rootstocks in a Station orchard designated as Crittenden 29R2T34,T35,T36. Subsequently, third and fourth clonal generations of trees were created utilizing buds for propagating wood taken from the Cr29R2T34 and Cr29R2T$_{35}$ trees for planting in 1982 at Cr31R5T5 and T6 and Lucey 50 R5T20,T21,T22,T23,T24 and T25 in 1987. These trees were observed, evaluated and harvested and also used as source material for propagating wood for distribution to collaborators in the USA, Canada, Belgium, France, Norway, Romania and Spain under restricted, nondistribution test agreements. Some of these trees have had research observations taken about their performance on a regular basis each year since 1966.

DESCRIPTION OF RELATED ART

In all test plantings, trees of NY 6476 (now named and released as 'Somerset') bore consistently heavy fruit crops as judged by experienced researchers and cherry orchardists. Some of these trees were tested during blossom time for pollenizer effectiveness and were found to belong to the pollenizer group designated as Group III (S3S4). Trees of 'Somerset' have been uniquely precocious in setting fruit earlier in their life time than many other sorts that we have had under test. 'Somerset' trees also have had a unique branching habit wherein they have lateral branches that are more numerous than most other cherry cultivars. This branching habit produces more opportunities for flower buds to form on previous season's growth leading to more non-spur fruiting than on most other sweet cherry cultivars that we have observed. The yield potential and realized crops of 'Somerset' cherries have been high when compared to cropping efficiency of other cultivars measured as weight of fruits divided by cross sectional area of trunk diameter.

There follows comparison of four traits of 29 sweet cherry cultivars and selections including 'Somerset' (NY 6476) originally published by Brown et al, *HortScience* 23:902–904. (1988):

For this study, a precise method for measuring both sweet cherry flesh and skin strength was required. The Instron Universal Testing Machine was chosen because it has been used to measure effectively components of firmness in fruit crops. The objective of the present study was to evaluate both total firmness (skin and underlying flesh) and flesh firmness of sweet cherry germ plasm by means of the Instron puncture test. We wanted to determine how effectively differences in these two components of firmness cound be detected within and between sweet cherry selections and cultivars. To provide a representative sample of material being used in breeding, standard cultivars were included in this study, along with several promising New York selections that were obtained by open pollination or from hybridizations between commercially important cultivars (Table 1). The objective was to assess the variability present within the breeding program for these components of firmness. The material being tested would also provide and objective assessment of how New York breeding selections compare with standard commercially grown cultivars.

Fruit and plant characteristics thought to be indicative of fruit maturity were also measured. These included fruit weight, the dimensions of the fruit (length, breadth, and width), soluble solids content (SSC) and fruit removal force (FRF). Correlations between these characteristics and fruit firmness were examined to determine if the firmness of the sample was related to the relative stage of maturity or to any of the other measured characteristics.

Fruit samples were obtained from trees grown in an orchard at the New York State Agricultural Experiment Station at Geneva. Since the optimum harvest date of sweet cherries is difficult to assess, previous performance records were used in an effort to ensure that selections and cultivars were harvested at the same relative stage of fruit maturity. The fruit size and color at harvest met commercial standards for the fresh market. Fruit were harvested at the red-mahogany stage as determined by reference to the cherry color comparator #6 (Tech West Enterprises, Ltd., Vancouver, B.C., Canada).

There follows comparison of four traits of 29 Sweet cherry cultivars and selections including 'Somerset' (NY6476) originally published by Brown et al, *HortScience* 23:902–904. (1988).

TABLE 1

Parentage of the Cultivars and New York Selections Evaluated

| Cultivar of Selection | Type[z] | Parentage |
|---|---|---|
| Bada | W | Unknown seedling × Ord |
| Bing | B | Republican open pollinated |
| Cavalier | B | Unknown |
| Early Rivers | B | Early Purple open pollinated |
| Emperor Francis | W | Unknown |
| Hedelfingen | B | Unknown |
| Hudson | B | Oswego × Giant |
| May Duke | D | Unknown (but sweet × tart cherry) |
| Merton Bounty | B | Elton × Schrecken |
| Merton Reward | B | Emperor Francis × Bedford Prolific |
| Moreau | B | Unknown |
| NY 1507 | B | Schmidt × Bing |
| NY 3308 | B | Windsor open pollinated |
| NY 3801 | W | Bing × NY 1495 [Emperor Francis × Gil Peck] |
| NY 5929 | B | Kristin [E. Francis × Gil Peck] × S. Hardy. Giant |
| NY 7679 | W | Pr. 1–638 × NY 5656 [E. Francis × Napoleon] |

TABLE 1-continued

Parentage of the Cultivars and New York Selections Evaluated

| Cultivar of Selection | Type[z] | Parentage |
|---|---|---|
| NY 9801 | B | Schneider open pollinated |
| NY 11390 | B | Chinook [Bing × Gil Peck] open pollinated |
| Rainier | W | Bing × Van |
| Sam | B | (Windsor open pollinated seedling) open pollinated |
| Schmidt | B | F. Schwarze Knopelkirsche open pollinated |
| Starkrimson | B | Stella × Garden Bing |
| Stella | B | Lambert [Napoleon × Black Heart] × J.I.2420 |
| Ulster | B | Schmidt × Lambert |
| Van | B | Empress Eugenie open pollinated |
| Victor | W | Windsor open pollinated |
| Viva | B | Ukendt × Victor |
| Windsor | B | Unknown |

[z]B = dark sweet cherry, W = white fleshed sweet cherry, D = duke

One random sample of 30 fruit was harvested from single trees of each cultivar or selection. Individual fruits were weighed and the length (base to apex), breadth (i.e. cheek), and width (i.e. suture) of each fruit was measured in millimeters. Fruit were then placed in refrigerated storage 4.5° C. for several hours before Instron testing to eliminate any variation due to temperature.

Fruit firmness was measured with the Instron Universal Testing Machine (Instron Corp., Canton, Mass.). Full scale load was set at 5. The crosshead speed was 5 $cm \cdot min^{-1}$, and chart speed 10 $cm \cdot min^{-1}$. Intact fruit was positioned so that the stem was in the horizontal plane. The skin of the fruit was punctured with a #41 drill blank (probe diameter 2.4 mm) on the area of the cheek to the right of the suture and the maximum force measured in newtons. Skin was removed from an adjacent area of the cheek on the opposite side of the suture and the same procedure was repeated to determine flesh firmness.

Fruit removal force (FRF), or the force required to remove the fruit from its stem, was determined using a Hunter mechanical Force Gauge (Ametek, Inc., Hatfield, Pa.). Fruit SSC was measured on the expressed juice of individual fruit with a hand-held refractometer.

All characteristics were analyzed by a one way analysis of variance (ANOVA) with cultivar being the variable. Means were separated by the method of LSD at the 5% level.

The ANOVA established significant cultivar effects for all fruit quality characteristics. The means for flesh and total puncture values, SSC, and fruit removal force are presented in Table 2. The cultivars and selections are arranged in order of their flesh puncture values, from the firmest (the highest value) to the softest.

Although fruit color is used commercially to gauge maturity, fruit removal force, fruit size, weight, and SSC are other important characteristics that can be used to assess fruit maturity. It was initially thought that some of the differences in firmness might be attributed to differences in maturity, but we found that the correlation between SSC and the flesh puncture value was not significant. The correlations between the flesh and total puncture values and FRF also were not significant (Table 3). This is evident when comparing firmness values of selections and cultivars with the same relative FRF, such as 'Van' and 'Hedelfingen' (Table 2).

TABLE 2

Means for Instron Puncture Values of Flesh Firmness and Total Firmness (skin and flesh combined), Soluble Solids Content (SSC), and Fruit Removal Force (FRF) of Sweet Cherry Cultivars and Selections

| Cultivar or Selection | Flesh (N) | Total (N) | SSC (% Brix) | FRF (g) |
|---|---|---|---|---|
| Moreau | 1.28 a[z] | 3.73 ef | 14.2 mn | 609 bc |
| NY 6476 | 1.21 ab | 4.17 bcd | 16.5 fgh | 422 f–j |
| Emperor Francis | 1.13 b | 4.44 ab | 17.4 cde | 550 d |
| Ulster | 0.97 c | 4.22 bc | 19.1 ab | 466 ef |
| NY 3801 | 0.97 c | 3.20 ijk | 13.7 n | 632 ab |
| Rainier | 0.95 c | 3.91 de | 17.0 d–g | 435 f–i |
| NY 9801 | 0.80 d | 3.77 ef | 18.9 ab | 419 g–k |
| NY 1507 | 0.79 d | 4.66 a | 19.4 a | 391 ijk |
| NY 5929 | 0.78 d | 3.18 ijk | 19.4 a | 342 lm |
| NY 3308 | 0.78 d | 3.21 ij | 15.9 hij | 489 c |
| Hudson | 0.77 de | 3.90 de | 17.7 cd | 569 cd |
| Bing | 0.76 de | 3.38 ghi | 19.1 ab | 326 m |
| Schmidt | 0.76 de | 3.42 ghi | 18.6 b | 397 h–k |
| Cavalier | 0.74 def | 3.93 cde | 15.5 jk | 465 ef |
| Van | 0.73 def | 2.78 mn | 18.9 ab | 436 fgh |
| Starkrimson | 0.72 d–g | 3.41 ghi | 14.0 n | 611 bc |
| NY 11390 | 0.69 c–h | 3.05 j–m | 19.4 a | 554 d |
| Sam | 0.66 f–j | 3.35 hi | 14.9 klm | 658 a |
| Bada | 0.63 g–j | 3.56 fgh | 17.3 cde | 430 f–j |
| NY 7679 | 0.62 hij | 3.20 ijk | 17.1 def | 270 n |
| Windsor | 0.58 ijk | 2.92 k–n | 15.8 ij | 419 g–k |
| Stella | 0.55 jkl | 3.21 ij | 16.0 hij | 573 cd |
| Victor | 0.54 jkl | 3.67 efg | 15.0 kl | 498 e |
| Viva | 0.51 klm | 3.13 i–l | 16.9 efg | 386 jkl |
| Hedelfingen | 0.49 klm | 2.88 lmn | 14.8 lm | 412 h–k |
| Merton Reward | 0.48 lm | 3.03 j–m | 16.4 ghi | 380 kl |
| May Duke | 0.43 mn | 2.67 no | 17.9 c | 501 c |
| Early Rivers | 0.42 mn | 2.34 p | 13.9 n | 460 efg |
| Merton Bounty | 0.39 n | 2.39 op | 17.0 d–g | 426 f–j |

[z]Means within a column separated by LSD, P = 5%. Each number is the mean value for 30 fruit.

The correlations presented are across all genotypes, but correlations within genotypes followed the same pattern. The lack of any large, significant correlations between firmness and the characteristics commonly used to indicate harvest maturity (Table 3) shows that the time of sampling did not bias the firmness results. Now that the use of the Instron for detecting differences in firmness has been established, the issue of determination of optimum harvest maturity can be addressed in future studies.

The correlations between puncture force and the other fruit characteristics were either not significant or below 0.35, indicating that indirect selection for firmness would not be feasible. The correlation coefficient of 0.49 between flesh and total puncture force values suggests that a high total puncture force does not ensure that flesh values will also be high (Table 3).

TABLE 3

Correlation Coefficients Between Fruit Characteristics Across 29 Genotypes of Sweet Cherry

| | Flesh | Total | SSC | FRF | Wt | Diam |
|---|---|---|---|---|---|---|
| Flesh | — | | | | | |
| Total | 0.49** | — | | | | |
| SSC | NS | 0.20** | — | | | |
| FRF | NS | NS | −0.32** | — | | |
| Weight | 0.22** | NS | NS | NS | — | |
| Diameter | 0.32** | 0.23** | 0.22** | NS | 0.96** | — |

NS/**Nonsignificant or significant at the 1% level, respectively.

The total firmness force value is not only an indication of skin strength, but is influenced by the firmness of the underlying flesh, so that the value obtained is a mixture of the two components. Therefore, when the percentage of flesh firmness to total firmness is calculated the values are surprisingly low, ranging from 15% to 34%. This does not suggest that the skin alone is responsible for the remaining percentage, but rather that it is the interaction of the skin and flesh.

When cultivars of similar total firmness are compared, the differences is flesh firmness can be large. This is found throughout the range of total firmness values as evidenced by the three pairs shown. The difference in the magnitude of flesh vs. total firmness has important implications in choosing cultivars for use in genetic improvement. A genotype with high flesh and high total values is preferred. Where genotypes have a high total value with a low flesh value, it is primarily the skin that is responsible for the perceived firmness. The strong contribution of skin to total firmness is evident in the case of NY 1507 and 'Victor' where the flesh accounts for only 17% and 15% of the total firmness, respectively. To emphasize the importance of flesh firmness to the perception of total firmness, 'Van' is regarded as being firm, yet in total firmness it ranks very low. However, the flesh is very firm and accounts for a relatively high percentage (26%) of the total value. The flesh texture of 'Van' may be responsible for its reputation for firmness.

Examination of Table 1 reveals that many commercial cultivars share a common parentage, with 'Napoleon' found several times in the pedigree of the firmer selections (Tables 1 and 2). The firmness values of several New York selections are higher than the commercial cultivars used in their development. Several New York selections are as firm as the commercially important 'Bing' in both total and flesh firmness with NY 6476, 'Somerset', being firmer than 'Bing' in both categories.

Use of the Instron not only allows us to identify those sources of firmness to be used in breeding, but also enables us to evaluate the progeny for both components of firmness. Studies of progenies resulting from hybridizations between the firmest cultivars and selections will provide greater understanding of the inheritance of firmness. This may aid the improvement in fruit firmness, which should greatly extend the storage life of the sweet cherry and result in improved fruit quality in the marketplace.

DESCRIPTION OF THE INVENTION

This invention relates to a new and distinctive cultivar of the cherry tree, 'Somerset', which we discovered in a test planting belonging to the New York State Agricultural Experiment Station, Cornell University, Geneva, Ontario County, N.Y. This discovery is a product of cherry breeding research program of the New York State Agricultural Experiment Station.

Pollination: We have conducted experiments to determine the pollination biology specifics about 'Somerset'. Our experiments took the form of field tests to cover the emerging flowers with paper bags and thereby isolate flowers of 'Somerset' from bee visitation. Such bagging allowed us to subsequently apply pollen derived from known sources to flowers' stigmas to determine the specific pollination compatibility group to which 'Somerset' belongs. It is self unfruitful and belongs to Group III as described by Crane and Brown, 1955. "Incompatibility and varietal confusion in cherries" *Sci. Hort.,* 11 pp. 53–55. This pollination group is rather common amongst commercially important sweet cherry cultivars. 'Somerset's' flowers contain ample amounts of viable pollen which is available for cross pollinaation via insect vectors. Flowers open early about one day before 'Bing' through the blooming time of sweet cherries in Geneva, N.Y. Although they bloom early compared to most other sweet cherry cultivars, they bear regular, heavy crops under all climatic conditions where they have been tested in various countries and states. Hence, we deduce that the ovaries of 'Somerset' flowers are highly fertile.

Detailed plant description: Immature leaves, flowers, fruit stems, pits and an intact tree with leaves and fruit thereon are shown in the figures which are individually described in the Brief Description of the Drawings section hereinbefore. The numerical color specifications employed in this patent disclosure are those of The Royal Horticultural Society Color Chart (1976).

Figure 1:
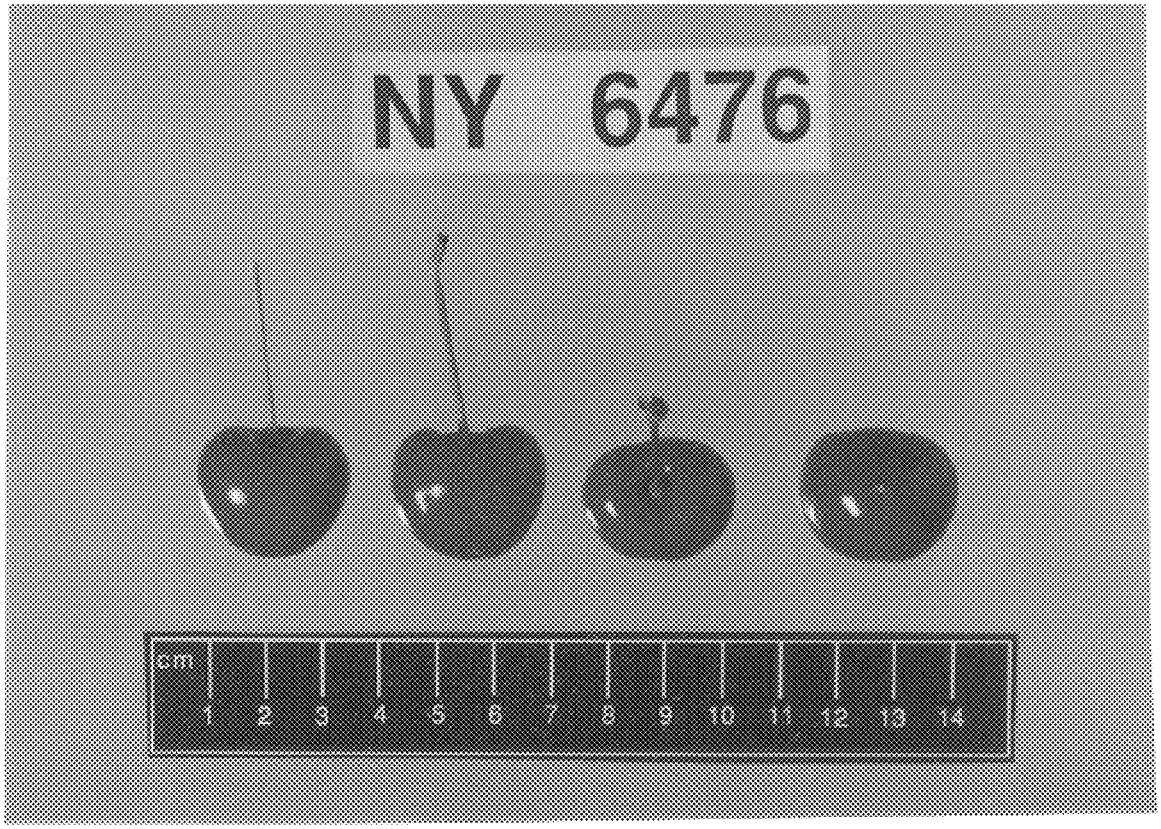
FIG. 1 is a photograph showing fruits and stems of 'Somerset' cultivar.
Figure 2:
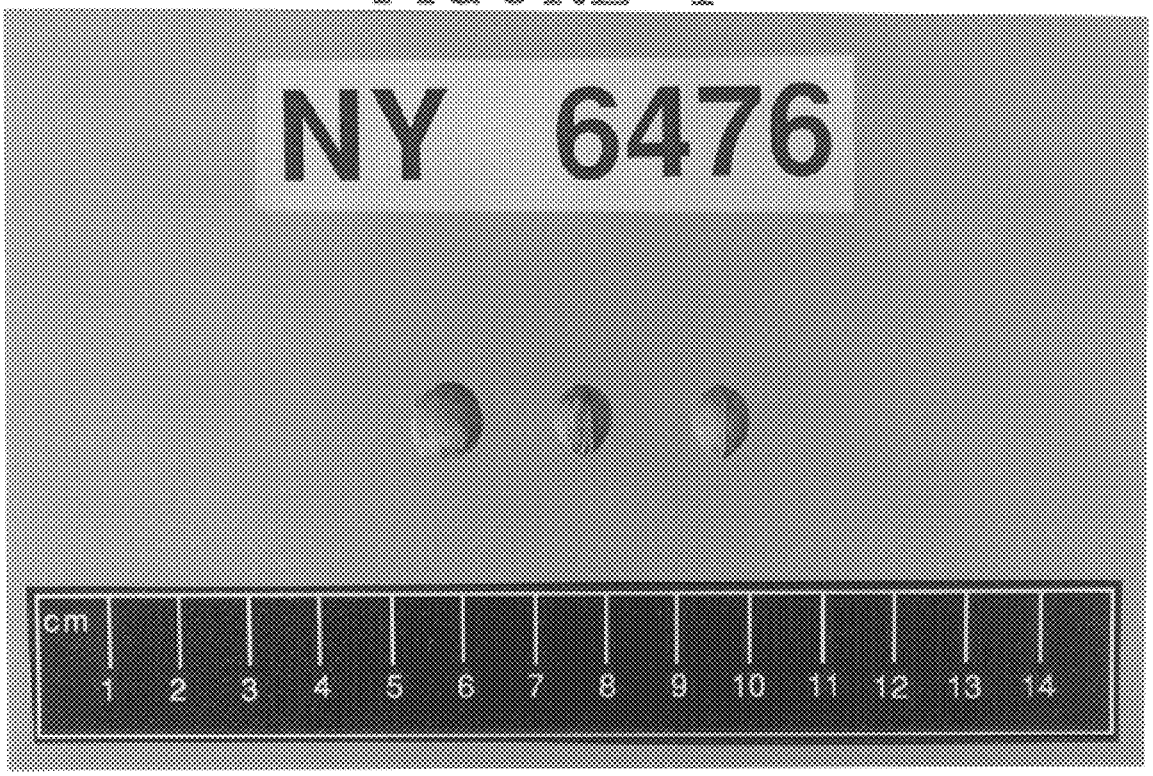
FIG. 2 is a photograph showing pits of fruit of 'Somerset' cultivar.
Figure 3:
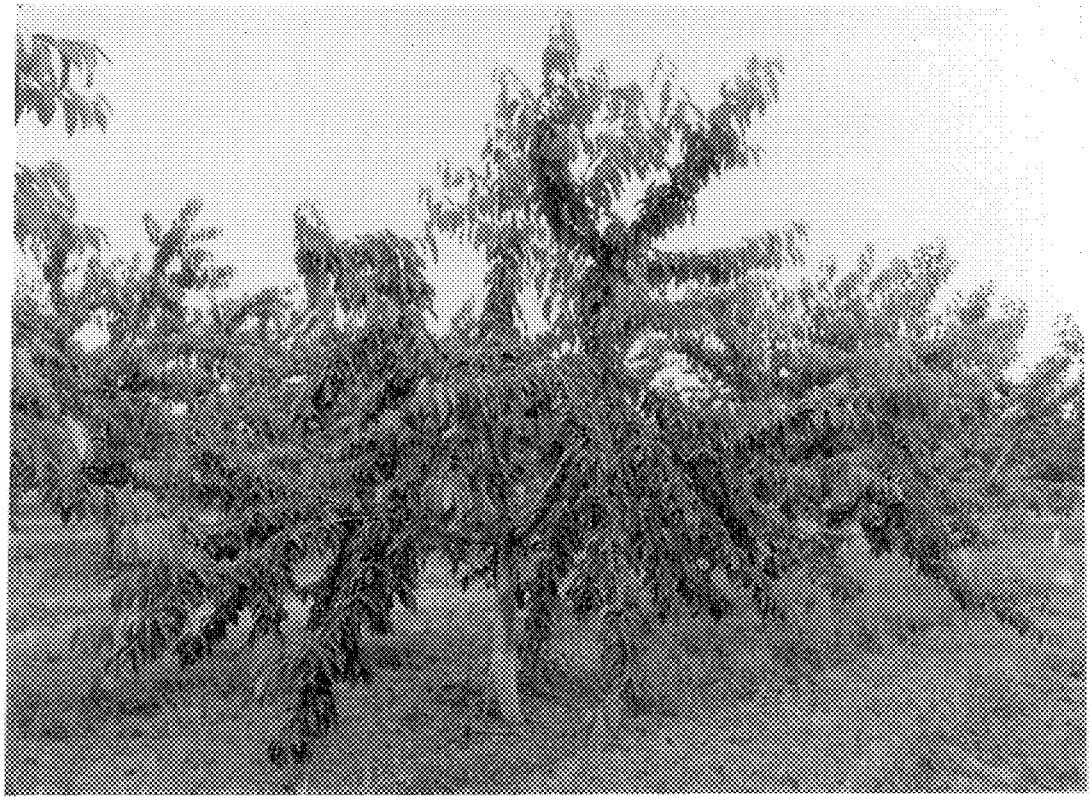
FIG. 3 is a photograph showing an intact tree with leaves and fruit thereon for 'Somerset' cultivar.
Figure 4:
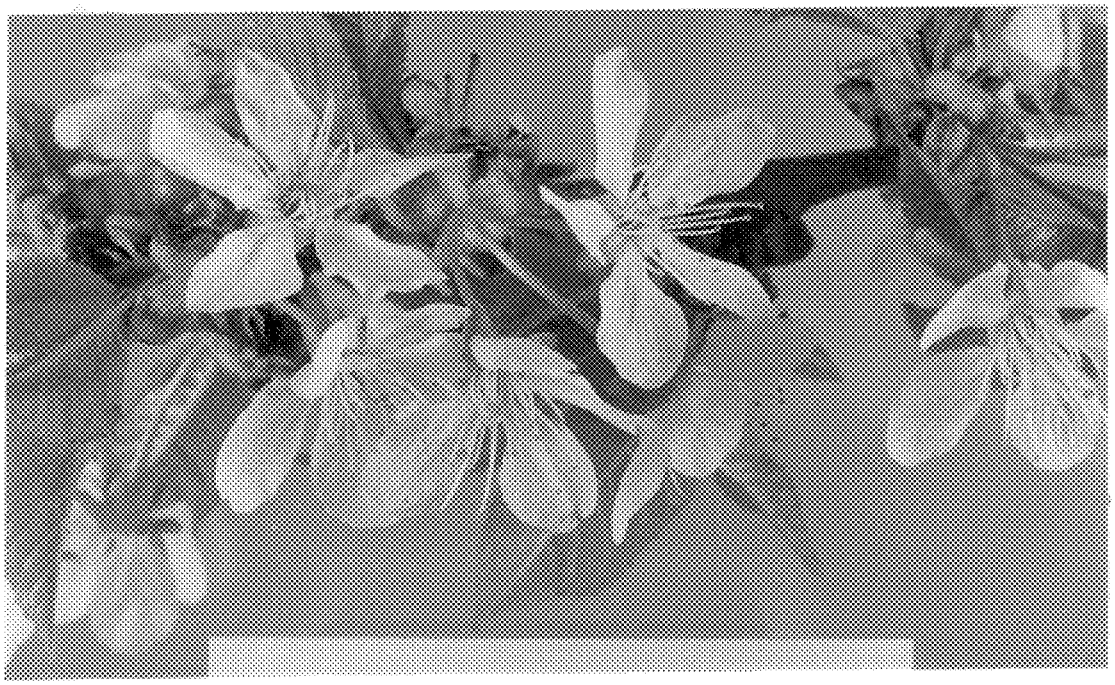
FIG. 4 is a photograph of a flower grouping and immature leaves for 'Somerset' cultivar.

Flowers and flowering: Flowers born on lateral branches or spurs on branches that are two years old or older (FIG. 4). They also are born from axillary buds of shoots laid down the previous growing season, more so than for most other cultivars that we have observed. Typically, 3 to 5 flowers are produced from spur buds and 3 to 5 flowers are also borne on proximal region axillary buds on the previous season's shoots.

Figure 5:
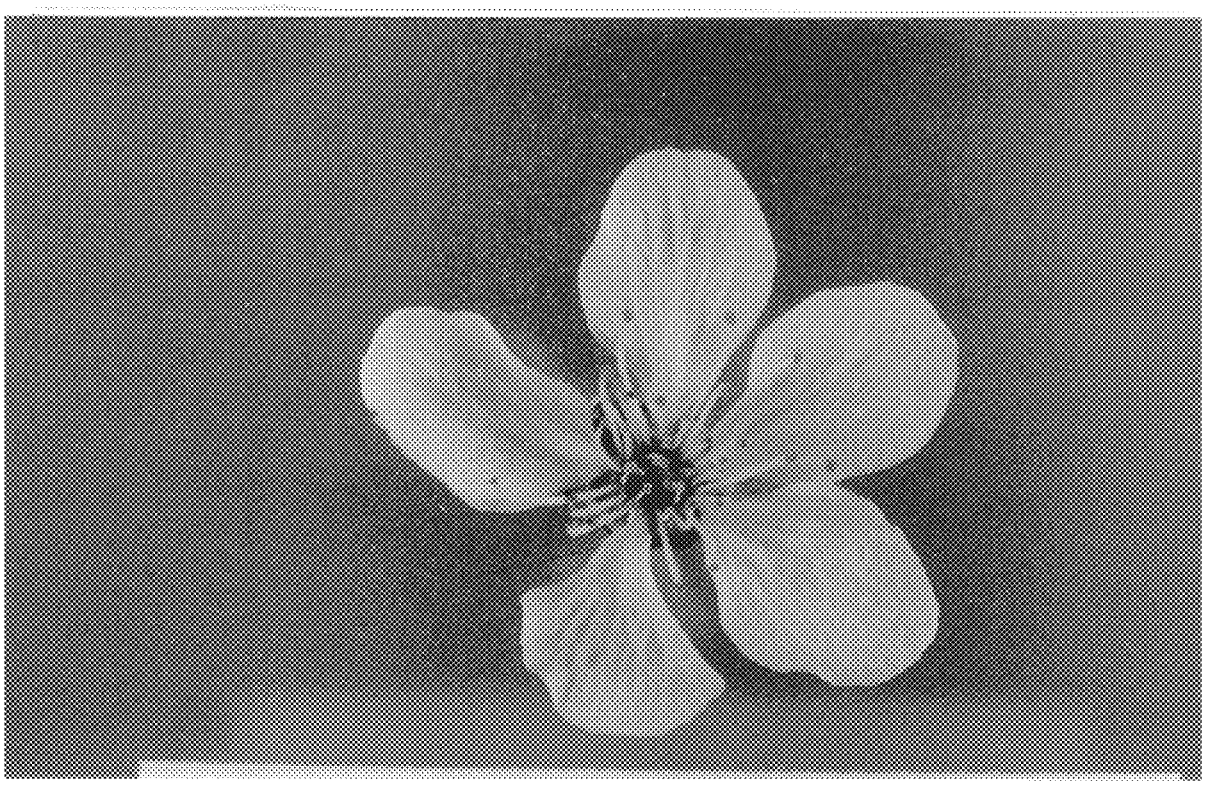
FIG. 5 is a photograph of a single flower of 'Somerset' cultivar.

Flowers (FIG. 5) are white, single and have no unusal features that distinguish them from those of other sweet cherry cultivars except that they open earlier than most other cultivars. They are structurally typical of *Prunus avium* with a base number of five petals and about 25 stamens. Pedicels are about 3.5 cm to 4.5 cm long and of intermediate thickness, about 1 mm. Anthers are yellow and pollen is yellow-orange. Self pollinations of 'Somerset' are unfruitful.

Fruiting habit and fruit: 'Somerset' trees which are grafted to the common cherry rootstock, 'Mazzard Seedling' (Mazzard), typically have flowers produced after only two growing seasons on trees that have been planted in their orchard position. Fruit is often set on trees which flower for the first time. This high precociousness to bear flowers and set fruit is a distinguishing feature of 'Somerset' when it is grafted to Mazzard.

The individual fruits of 'Somerset' are cordate (slightly heart shaped), their skin color at maturity is greyed-purple 187A with a high sheen. Their flesh color is a slightly lighter shade of greyed-purple, 187B. Fruits are very symmetrical, and medium large compared to most other sweet cherry cultivars. They are about 2.7 to 3.1 cm in diameter of width and 2.4 cm to 3.0 cm long. The pits are round conic with size being medium about 1.1 cm long and 1.0 cm wide across the suture and 80 mm wide in their flatter dimension with slightly protruding tips on the stigmatic ends. A typical fruit is shown in an accompanying photograph. Fruits of 'Somerset' resist moisture stress induced cracking better than the 'Bing' cultivar. The soluble solids level of 'Somerset' fruit is generally above 17 percent and always above 16 percent at maturity in Geneva. The natural acidity level of 'Somerset' fruits is higher than many commercially important cultivars. The flavor of 'Somerset' fruits is stronly cherry-like and the good balance of natural sugars and natural acidity makes the quality of its fruit particularly appealing to people who prefer tartness in sweet cherry taste. Their flesh is firmer than most other sweet cherry cultivars, about 1.21 Instron units at maturity. They have a fruit removal force at maturity of about 422 grams of pull force. Fruit ripening is about with the 'Hedelfingen' and 'Lapins' cultivars, which is about 65 days after full bloom in Geneva.

Tree habit: 'Somerset's' tree habit is low in vigor, spreading with many lateral branches produced along apical portions of about 30% of the previous season's growth. This tree habit and branching structure leads to a round form to the tree crown in mature, unpruned fruiting trees. The trees of 'Somerset' produce more lateral limbs that emerge at wider angles to the trunk and to scaffold limbs than most commercial cultivars including 'Bing,' 'Napoleon,' 'Rainier,' 'Emperor Francis,' 'Sam,' 'Hedelfingen,' and 'Van.' The lateral limbs are very strongly connected. 'Somerset' has never been observed by the inventors to have limb breakage problems even with its heavy cropping capacity. It is a subjective observation that the wide angles of the scaffold limbs and secondary scaffold limbs contribute to the strong crop carrying capacity of 'Somerset' trees. 'Somerset' trees are slightly less vigorous than most commercial cultivars of sweet cherries and are naturally about 20% smaller than the trees of most commercial cultivars of sweet cherries at 10 years of age. The height and width are expediently held to 10 to 11 feet by pruning.

Shoots: 'Somerset's' shoots are of medium length with many lateral branches. They have small lenticels. In the autumn after cessation of terminal growth, the color of the bark at the fourth internode above the proximal position is greyed-orange 165A on the side of the stem which is commonly exposed to direct sunlight. The other side of the stem is greyed-yellow 161A. The sun exposed color contrasts to greyed-orange 165B in the 'Bing' cultivar.

Leaves: Leaves of 'Somerset' are medium in leaf area, usually symmetrical, lamella glabrous and smooth with adaxial lamella surface dark yellow-green 137A, abaxial surface yellow-green 147B and margins of mature leaves are usually coarsely double serrate with two primary serrations per cm, glands are reniform and averaging 2 per petiole, stipules are present during early stages of growth but abscise before fruit maturity, petioles 3 to 3.75 cm long, leaf position typically 65 to 75 degrees from the perpendicular shoot.

Bark: At Geneva, N.Y., the color of the bark on the north side of the trunks of mature fruiting trees at 50 cm. above the soil line is Greyed-Purple 187B while the 'Bing' cultivar has slightly darker bark, namely Greyed-Purple 187A. 'Somerset' has elliptical lenticels that are larger in both length (three to five times longer) and height (about twice the height) than those of 'Bing.' the lenticels have a line or crack running the full length near their center. They often form a chain that is continous around a high percentage of the circumference of the trunk, whereas, in 'Bing,' they are discontinous and much less frequent so that much more smooth bark is present on the lower trunk 'Bing' than on 'Somerset' so the mature bark of 'Somerset' has more and larger lenticels and a somewhat rougher texture than the mature bark of 'Bing.' The lenticels of young trees tend to hold the same pattern as they mature.

Rootstocks: 'Somerset' trees have shown two characteristics that help delineate them as unique when grafted and grown on rootstocks in New York. The 'Somerset' scion causes root suckers to emerge from trees grafted to 'Mazzard Seedling' under Geneva orchard conditions. Although a few other varieties have a low incidence of this trait in Geneva, 'Somerset' nearly always has this feature. When grafted to 'Damil,' a cherry rootstock cultivar known to induce genetic incompatibility between the scion and rootstock tissues in many sweet cherry scion cultivars in New York conditions, 'Somerset' has not shown typical delayed incompatibility symptoms (reduced lateral branching, yellow-green leaves, premature "flagging" (drooping) of leaves and early cessation of annual growth and premature tree death).

Training and pruning: 'Somerset' requires much less attention to cultural manipulations like the use of scoring of the bark and growth regulator applications to induce limb emergence than most commercial cultivars. No special manipulations are required to spread the angle of the emerging limbs to a more horizontal position. Precocity of young trees is so high that early cropping tends to pull the limbs down into a habit or tree form that is conducive to heavy flower bud initiation and very high fruit set and yield potential. Because 'Somerset' produces a smaller tree compared to most commercial cultivars, 'Somerset' trees can be planted at about 20–25% closer spacings in most orchard systems than can commonly grown commercial cultivars. Pruning for renewal of fruiting woods is somewhat greater for 'Somerset' than is necessary for most commercial cultivars that have less branching and later and lighter croppping. For the home gardner/orchardist, the unique characteristics of ease of training and smaller tree size on comparable rootstocks allow for better utilization of lawn/yard/garden space and earlier production of home grown fruit. Although 'Somerset' has a tendency in some years to overset its cropload and then produces smaller fruit size in that season, there are no known cultural practices that thin crop load besides heavy pruning to cut off limbs that would have born "extra" fruit. The pull force for 'Somerset' is satisfactory for harvesting by commercial processing operations.

Usefulness

'Somerset' sweet cherry is well suited for production to fulfill certain fresh market demands in most major sweet cherry production regions of the USA and other countries. The particularly favorable features of this cultivar are its firm, attractive, good flavored fruit, borne precociously on a uniquely branching tree. The tree's precocity coupled with its fruiting profusely on both spurs and previous season's growth and its affinity for some size contolling rootstocks make it desirable for high density orchard plantings, a much needed approach for more profitable sweet cherry production in some areas of the world. 'Somerset' will require a pollenizer cultivar interplanted with it which will bloom at the same, early flowering season and which is not in the Group III pollination category. In our field observations of 'Somerset' we have noted better tolerance to rain induced fruit cracking than most other cultivars with comparable fruit firmness. Thus, the inventors believe that 'Somerset' is highly likely to replace the primary mid-late season cultivar in the Great Lakes Region, 'Hedelfingen,' because it has higher yields of firmer more attractive fruit.

The productivity of 'Somerset' was among the top five of 16 sweet cherry cultivars tested and the 16 cultivers were selected for further screening from over 50 cultivers. In the same test, 'Somerset' tied for first in firmness and its percent cracked fruit is amongst the lowest.

Disease and pest resistance: In those cases where 'Somerset' clusters, it is more susceptible to brown rot than most other commercially grown cultivars of sweet cherry but not more susceptible to brown rot than several newer self-fertile cultivars including 'Stella,' Lapins' and 'Vandalay' and ultra heavy setting self-incompatible cultivars like 'Van' which suffer from brown rot infections as much or more than 'Somerset.' In seasons where rains occur during final fruit maturation, 'Somerset,' with its somewhat higher tolerance to rain-induced fruit cracking has less incidence of brown rot than commercially important, highly crack-susceptible cultivars such as 'Van.' Turning now to leaf infections, 'Somerset' has greater susceptibility to leaf infections caused by the bacteria *Pseudomonas syringae* than do the commercially important cultivars 'Emperor Francis,' 'Starks Gold,' 'Sam,' 'Hedelfingen,' 'Rainier,' and 'Van,' but less susceptibility to leaf infections than 'Bing,' 'Napoleon,' 'Lapins,' and 'Newstar.' The tolerance of 'Somerset' to wood/bark infection is rated as better than that of 'Rainier,' 'Van,' 'Bing,' 'Napoleon,' 'Lapins,' and 'Newstar' based on experiments at Geneva, N.Y. Turning now to X-disease, 'Somerset' is less tolerant to X-disease than the two cultivars existing with tolerance to X-disease, namely 'Sweet Ann' and 'Angela,' but these two cultivars are not commercially viable. Susceptibility to other graft transmissible pests is not known for 'Somerset.' To fulfill the need for uninfected propagating stocks, 'Somerset' has been indexed by the Washington State University NRSP5 Project at Prosser, Wash. and uninfected propagating stocks are supplied to commercial nurseries. No known difference in tolerance to insects and nematode pests exists for 'Somerset.'

Other cultivars: The 'Cavalier' and 'Starkrimson' cultivars mentioned in the tables hereinbefore are known to be patented in the United States. The other cultivars listed in said tables that have names and not numbers are known to have been released for commerce without plant patent protection. So far as the numerical accessions in the tables are concerned, NY3308 and NY11390 are the subject respectively of U.S. Plant patent application Ser. Nos. 08/835,640 and 08/831,762.

What is claimed is:

1. A new and distinct cultivar of sweet cherry tree substantially as herein described and illustrated.

* * * * *